United States Patent [19]

Grossberg et al.

[11] 4,252,791
[45] Feb. 24, 1981

[54] INTERFERON STABILIZATION

[75] Inventors: Sidney E. Grossberg, Whitefish Bay; Joseph J. Sedmak, Milwaukee, both of Wis.

[73] Assignee: The Medical College of Wisconsin, Inc., Milwaukee, Wis.

[21] Appl. No.: 86,297

[22] Filed: Oct. 19, 1979

[51] Int. Cl.³ .................. A61K 45/02; A61K 37/00; A61K 39/00
[52] U.S. Cl. .................. 424/85; 424/177; 260/112 R
[58] Field of Search .............. 424/85, 92, 177; 260/112 R

[56] References Cited

U.S. PATENT DOCUMENTS

| 3,981,991 | 9/1976 | Stewart et al. | 424/85 |
| 4,100,150 | 8/1978 | Cartwright | 260/112 R |

OTHER PUBLICATIONS

Jariwalla, R., et al., Archives of Virology, vol. 49, pp. 261-272, 1975.
Epstein, L., et al., J. of Immunology, vol. 112, No. 2, pp. 617-626, 1974.
Sedmak, J., et al., J. of Gen. Virol., "Interferon Stabilization and Enhancement by Rare Earth Salts," In Press.
Jariwalla, R., et al., J. Gen Virol., vol. 35, pp. 45-52, 1977.
Rubinstein, M., et al., Proc. Natl. Acad. Sci., vol. 76, No. 2., pp. 640-641, 1979.
Berman, B., and Vilcek, J., Virology, vol. 57, pp. 378-386, 1974.
Edy, V., et al., J. Gen. Virol., vol. 33, pp. 517-521, 1976.
Cantell, K., et al., Proc. of the Tissue Culture Association Work Shop, Lake Placid, N.Y., 35-38, 1973.
Heine et al., Archives of Virology, vol. 57, p. 185, 1978.
Jameson, G., et al. Grossberg, Cryobiology, vol. 16, p. 301, 1979.
Knight, Cell Biology, vol. 73, p. 520, 1976.
Sedmak, J. and Grossberg, Human Interferon Production and Clinical Use, Slinebang & Chapple(eds) pp. 133-152, 1978.
Sedmak & Grossberg, Texas Reports on Biology and Medicine, vol. 35, p. 198, 1977.

*Primary Examiner*—Delbert R. Phillips
*Assistant Examiner*—Blondel Hazel
*Attorney, Agent, or Firm*—Quarles & Brady

[57] ABSTRACT

The loss of biological activity of interferons is prevented or reduced by the addition of soluble lanthanide or calcium salts.

22 Claims, No Drawings

INTERFERON STABILIZATION

TECHNICAL FIELD

This invention relates to the stabilization of interferons so as to reduce their loss of biological activity.

BACKGROUND ART

The numbers which appear in brackets throughout the following description refer to the List of References found at the end of the description. Reference [1] is an excellent current review of interferons with articles relating to various aspects of the interferon system. Reference [2] is an older book which reviews interferon research.

Interferons are natural cell products produced by appropriately stimulated vertebrate cells that provide antiviral resistance against many different kinds of viruses. The currently accepted criteria for an interferon include: (a) differentiation from nonspecific toxic effects on cells which would otherwise limit virus growth; (b) inhibitory effects on a range of unrelated viruses; (c) demonstration of intracellular effects requiring protein and ribonucleic acid synthesis; (d) loss of biological activity after proteolytic enzyme treatment e.g., trypsin; (e) relative species specificity; (f) neutralization of its biological activity by specific antiserum; (g) a protein of molecular weight between 12,000 and 45,000, although some have even greater molecular weights; (h) relative stability at low pH; and (i) relatively high specific activity in relation to protein concentration. Specific characteristics of interferons from different animal species or cells may differ from one another.

While it is known that, as against viral infections, interferon acts intracellularly to limit viral synthesis, the mechanism by which this is accomplished has not yet been established precisely. The action of interferon is not to inactivate directly the virus particles, but to make the cell resistant to virus infection in some indirect manner. Interferon appears to bind to cell surface receptors and require cellular metabolic activity for expression of such resistance, especially ribonucleic acid and protein synthesis. Thus, it is generally accepted that the action of interferon in a cell is to induce the synthesis of another protein which appears to act at the ribosomal level to interfere with the synthesis of viral-coded, functional enzymes and structural coat proteins necessary for viral replication. It is generally true that interferon is most active in cells of the same animal species from which it was produced, but instances are known of family or order crossreactivity and are reported in the literature.

Interferon production by a cell, in either a suitable culture or in an intact animal, is stimulated by a variety of agents referred to as "inducers". A large number of animal viruses are known to be effective as interferon inducers, although not all viruses induce interferon production. Examples of viruses effective as interferon inducers are influenza, Newcastle disease, and Sendai viruses. Nonviral interferon inducers are also known, including both natural and synthetic products. The natural products, mostly of microbial origin, include nucleic acids, especially double-stranded RNAs; intracellular microbes such as bacteria, ricksettia and protozoa; and microbial products such as lipopolysaccharides and protein. Some of the synthetic inducers include synthetic RNAs, such as poly rI-poly rC; polymers such as polyacrylic acid and polysulfates; and low molecular weight substances such as cycloheximide, tilorone, and basic dyes. A more complete listing of natural and synthetic nonviral inducers is set forth in Reference [3].

Interferons are said to have been discovered by Isaacs and Lindenmann in 1957 [4; see 5 & 6]. Since that time, there has been considerable research directed towards the investigation of the clinical use of interferons, particularly human interferon. However, this has been inhibited by the limited availability of interferon in sufficient quantities to enable large scale clinical investigation, and it is only within the last few years that the pace of such work has accelerated. Interferon has been demonstrated to be effective in limiting several experimental viral infections of animals, a number of infectious agents have been shown to be inhibited by a variety of materials known to be interferon inducers, and experiments in vitro and with laboratory animals have revealed interferon exhibits antitumor activity; see the literature reviewed in Reference [3]. Reference [7] presents the results of a workshop convened by the National Institute of Allergy and Infectious Diseases and the National Cancer Institute on Mar. 21-23, 1978 which reviewed the information from clinical trials of exogenous interferon in the treatment of both infectious and metastatic diseases. Other of the references attest to the current high degree of interest in the examination of the clinical use of interferon, [8,9]. Effective interferon treatment has been reported for herpesvirus infections, hepatitus B infections and respiratory virus infections, as well as osteogenic sarcoma, lymphoma, breast cancer, multiple myeloma and leukemia. The interest in interferons and the fact that relatively large amounts are required for many clinical uses has created a need for large-scale interferon production methods, which in turn results in a need for an effective method of stabilizing interferons against loss of biological activity during and after production.

A number of techniques for the production of interferons from various types of cells are described in the literature; see e.g. [11, 12, 13 & 14]. In general, the procedures involve the following stages:

(1) Cell collection and purification. Human interferon is produced from leukocytes obtained from blood centers, diploid fibroblasts usually obtained from infant foreskins, and lymphoblastoid cells, generally of the Namalva cell line.

(2) Induction of the cells with a suitable inducer, often preceded by priming with interferon or followed by superinduction in the production of fibroblast interferon.

(3) Incubation of the induced cells in a suitable medium for a sufficient time to produce interferon.

(4) Purification and concentration of the crude interferon. Classical purification procedures such as acid precipitation, dialysis, molecular sieve chromatography, isoelectric focusing, and affinity chromatography have been employed to purify interferons. Purifications, presumably to homogeneity, have been recently reported, for human interferons to $2 \times 10^8$ units/mg of protein, and for mouse interferon $1 \times 10^9$ units/mg of protein.

(5) Safety testing of the interferon.

(6) Storage of the interferon prior to and during clinical administration.

The cell cultures are typically incubated in suspension or as a monolayer in roller bottles [12], although recent work has described the use of microcarrier beads electrically charged to attract and hold the cells [8]. At various stages the interferon is subjected to mechanical stress, such as imposed by stirring and filtration, or thermal conditions which can result in inactivation of the interferon; this can often occur during the purification and concentration, safety testing and storage stages. Human fibroblast interferon is particularly subject to inactivation by heat and mechanical stress. Human leukocyte interferon is more stable than fibroblast interferon and has generally been regarded as being a relatively stable molecule, but it is now known that losses in activity especially occur in very dilute solutions containing low concentrations of protein. Our paper [10] and its references contain more detailed information regarding the inactivation of interferons.

The prior art techniques for the stabilization of interferons include the following:

(a) Human leukocyte interferon can be stabilized against thermal inactivation by sodium dodecyl sulfate (SDS). However, SDS binds tenaciously to proteins and is almost impossible to remove, which lessens its clinical usefulness.

(b) Freeze drying of interferons can limit loss of activity during storage. This is useful only for storage and cannot be used during the processing of interferons.

(c) U.S. Pat. No. 3,981,991, Stewart & deSomer, relates to the stabilization of interferons using a combination of three compounds: an agent such as urea for disrupting non-covalent bonds; an agent such as mercaptoethanol for reducing disulfide bonds; and an anionic or cationic surface-active agent such as SDS.

(d) U.S. Pat. No. 4,100,150, Cartwright, relates to the stabilization of interferons with thioctic acid, which acts to reduce sulfhydryl (—SH) groups of the interferon without reducing its disulfide (—S—S—) linkages.

(e) It has been reported that human fibroblast interferon can be stabilized for long term storage at 4° C., with ethylene glycol [22].

We have now found a new technique for interferon stabilization which employs compounds not heretofore known to be effective for stabilizing interferons.

DISCLOSURE OF THE INVENTION

Our present invention is based upon our discovery that lanthanide and calcium salts effectively enhance the stability of interferons. We have found that the lanthanide and calcium salts can be added to solutions of interferons and will aid in the preservation of the interferons' biological activity when subjected to thermal and mechanical stress. The enhanced stabilization provided interferons by these compounds, as demonstrated by the experimental data presented in the ensuing disclosure, will enable interferons to better withstand the stresses imposed during their production and storage; this is accomplished without impairing their potential clinical utility.

Our invention thus relates to a composition of matter comprising a solution of an interferon and a soluble lanthanide or calcium salt present in a stabilizing amount. The term "lanthanide" refers to the elements of Group III B of the Periodic Table of the Elements from lanthanum through lutetium; these elements have atomic numbers from 57 to 71 inclusive and are generally referred to as the Lanthanide Series.

In addition to their stabilizing effect, we have found that the lanthanide salts also appear to increase the biological activity of the interferons.

DESCRIPTION OF BEST MODES FOR CARRYING OUT THE INVENTION

A number of specific examples illustrating the stabilization of interferons in accordance with our present invention are set forth below. The sources of the interferons and rare earth chemicals, assays and test procedures used in Examples 1–26 are described first.

(a) Interferons (1) Human Fibroblast Interferon—Lot A. One interferon lot supplied by National Institute of Allergy and Infectious Diseases was induced by Dr. Vilcek in human foreskin cells using poly I. poly C as the inducer and sequential treatment with cycloheximide and actinomycin D to increase the interferon yield [15] and then was purified by C. Anfinsen by immunoaffinity chromatography [16]. This preparation when made up in 0.05 M citrate pH 2.2, contained 500 μg/ml of added cytochrome C, and had a specific activity of $1.6 \times 10^6$ units per mg. of protein considering the cytochrome C concentration. This interferon is sometimes referred to as HFI-A hereinafter.

(2) Human Fibroblast Interferon—Lot B. The second lot of fibroblast interferon was a controlled-pore-glass-purified human fibroblast interferon supplied by Dr. Edy [17]. The purified preparation contained $10^{5.3}$ units/ml of interferon and had a protein content of 28 μg/ml. This interferon is sometimes identified as HFI-B hereinafter.

(3) Human Leukocyte Interferon. A purified preparation of human leukocyte interferon was obtained from Dr. Cantell [18]; it had $200 \times 10^6$ units/ml of interferon and 42 mg/ml protein. This interferon is sometimes hereinafter referred to as HLI.

(4) Mouse Interferon. The mouse interferon used was a crude preparation of Newcastle disease virus induced in L-cells [19] with a specific activity of $10^4$ units per mg protein. This interferon is sometimes identified as MI in the following disclosure.

(5) Immune-Induced Human Interferon. Crude immune-induced human interferon from phytohemagglutinin stimulated lymphocytes and macrophages was obtained from L. Epstein [20]. This preparation had a specific activity of 54 units/mg protein. This interferon is sometimes identified as IHI in the balance of this disclosure.

(b) Interferon Assays

Human interferon potency was measured by the degree of inhibition in the yield of encephalomyocarditis (EMC) viral hemagglutinin in human skin Bud-8 cells [21]. This assay measures about 9 times the 20,000 units assigned to the NIH human leukocyte interferon standard G023-901-527 and about 7 times the 10,000 units assigned to the NIH human fibroblast standard G023-902-527.

Murine interferons were assayed by measuring the inhibition of yield of GDVII viral hemagglutinin in mouse $L_{929}$ cells [19]. This assay measures the same unitage, 12,000 units/ml, as that assigned to the NIH mouse reference interferon standard G002-904-511.

The term "units" as used in Examples 1–26 with respect of interferons means the reciprocal of the dilution of interferon which results in a $0.5 \log_{10}$ reduction in the yield of viral hemagglutinin, [21].

(c) Rare Earth Salts

All of the rare earth salts were obtained from Apache Chemicals, Inc., Seward, Ill.

(d) Stability Tests

Thermal stability was determined by an accelerated isothermal heating test usually at 37° C. but higher temperatures (50° C. and 56° C.) were used for the human leukocyte preparation. Samples (0.5–1.0 ml) were heated for various lengths of time ranging from 1 to 4 days, frozen at −70° C. and then thawed just before assaying for antiviral activity. The antiviral activity of a sample after being subjected to the heating test was compared to its antiviral activity prior to the heating test to determine the extent to which the sample resisted inactivation by heat.

Mechanical stability was determined by subjecting samples to vigorous agitation at full speed with a Lab-line Instruments, Inc. vortex action mixer. Samples (0.5–1.0 ml) in glass or plastic vials were agitated at 4° C. in 30-second bursts so that the sample would not be heated by friction. The antiviral activity of a sample was assayed before and after the application of the mechanical stress to determine the extent to which it resisted inactivation by mechanical stress.

In the following Examples 1–26, an interferon solution was mixed with a sufficient amount of a lanthanide or calcium salt solution such that the final concentration of the lanthanide or calcium salt in the resultant solution was at the values shown in the examples and tables. In the case of the immune-induced interferon of Example 24, however, the interferon was dialyzed against a calcium salt solution of the indicated concentration. In all cases, the concentration of the lanthanide or calcium salt set forth in Examples 1–26 and Tables 1–8 and in the following description means the final concentration of the lanthanide or calcium salt in the resultant solution of an interferon and the salt. A solution of Tris (hydroxymethyl) amino methane when used as a buffer in the examples was neutralized to the indicated pH by the addition of HCl, and the neutralized solution is referred to as Tris-HCl in the following description. Unless otherwise indicated, the Tris-HCl was used as a buffer at a 0.05 M concentration and a pH of 7.2. The term "titer" where used hereinafter means the number of units of interferon per ml of the resultant solution of interferon and lanthanide or calcium salt, i.e. units/ml.

Examples 1–12 show the stabilization of human fibroblast interferons against thermal inactivation and examples 13–20 illustrate their stabilization against mechanical stress using various lanthanide chlorides; example 21 illustrates the use of calcium chloride as a stabilizer; examples 22 and 23 demonstrate lanthanium acetate as a stabilizing agent against thermal and mechanical stress, respectively; example 24 shows the stabilization of other types of interferons; example 25 presents data regarding long term stabilization; and example 26 establishes the utility of various buffers with the stabilizing compounds and their effectiveness over a wide pH range.

EXAMPLES 1–8

Solutions of the human fibroblast interferon—Lot A, part (a)(1) above, with chloride salts of 8 different lanthanides were made up to contain lanthanide salt concentrations of 0.01 M and 0.002 M. The solutions included Tris-HCl, pH 7.2, as a buffer. The antiviral activity of the HFI-A in each solution was assayed after mixing, after 1 day of heating at 37° C. under the thermal stability test (part d above), and after 4 days of heating at 37° C. to determine the percentage of antiviral activity remaining at each time period. The lanthanides used in these salts have an atomic number ranging from 57 to 70.

The results of these examples are set forth in Table 1. The "control" listed in Table 1 was a solution of the HFI-A in a Tris-HCl buffer, pH 7.2.

The data of Examples 1–8 demonstrate that the lanthanide salts were very effective in stabilizing the purified human fibroblast interferon against thermal inactivation. The almost complete inactivation of the control sample after heating for either 1 day or 4 days would render the interferon useless for any purpose, whereas the interferon when treated with the lanthanide salts would remain useful after being subjected to the same thermal conditions.

TABLE 1

Thermal Stability of HFI-A in Presence of Lanthanide Salts

| Ex. | Lanthanide Salt | 0 days | 1 day | 4 days |
|---|---|---|---|---|
| | | | Titer at indicated days of incubation; % of initial activity remaining after heating shown in ( ) | |
| 1. | Lanthanum Chloride - 0.01M | 12,000 | 9,000 (75%) | 7,000 (58%) |
| | Lanthanum Chloride - 0.002M | 12,000 | 12,000 (100%) | 5,000 (42%) |
| 2. | Cerium Chloride - 0.01M | 17,000 | 12,000 (71%) | 12,000 (71%) |
| | Cerium Chloride - 0.002M | 17,000 | 17,000 (100%) | 7,500 (94%) |
| 3. | Neodymium Chloride - 0.01M | 7,000 | 7,000 (100%) | 7,000 (100%) |
| | Neodymium Chloride - 0.002M | 7,000 | 7,500 (107%) | 7,500 (107%) |
| 4. | Samarium Chloride - 0.01M | 17,000 | 14,00 (78%) | 17,000 (78%) |
| | Samarium Chloride - 0.002M | 17,000 | 20,000 (118%) | 17,000 (100%) |
| 5. | Gadolinium Chloride - 0.01M | 13,500 | 7,000 (53%) | 7,100 (58%) |
| | Gadolinium Chloride - 0.002M | 24,000 | 19,000 (79%) | 19,000 (79%) |
| 6. | Dysprosium Chloride - 0.01M | 30,000 | 24,000 (80%) | 20,000 (67%) |
| | Dysprosium Chloride - 0.002M | 20,000 | 17,000 (85%) | 17,000 (85%) |
| 7. | Erbium Chloride - 0.01M | 20,000 | 17,000 (85%) | 17,000 (85%) |
| | Erbium Chloride - 0.002M | 20,000 | 20,000 (100%) | 17,000 (85%) |
| 8. | Ytterbium Chloride - 0.01M | 20,000 | 20,000 (100%) | 20,000 (100%) |
| | Ytterbium Chloride - 0.002M | 17,000 | 17,000 (100%) | 12,000 (71%) |
| | CONTROL | 5,000 | 800 (16%) | less than 2.5% |

The solutions of Examples 1–8 and the control solutions were prepared with the same volume of stock interferon solution having an assayed activity of 5,000 units/ml.

EXAMPLES 9-11

The human fibroblast interferon—Lot B, of part (a) (2) above, which is more highly purified than the HFI-A, was also effectively stabilized against thermal inactivation by the addition of lanthanide salts. Solutions of the HFI-B were mixed with lanthanide chloride solutions to produce final solutions having lanthanide chlorides at the indicated concentrations along with 0.05 M Tris-HCl, pH 7.2, as a buffer. The antiviral activity of each solution was measured before the thermal stability test at 37° C., after 1 day of heating, and after 4 days of heating; the data are recorded in Table 2 in terms of the titer and percentage of remaining activity. The "control" solution for Table 2 was HFI-B in 0.05 M Tris-HCl buffer, pH 7.2.

The data of these Examples show the lanthanide salts to effectively stabilize the HFI-B against thermal inactivation at a concentration of 0.002 M, a lesser but still useful degree of stabilization at a concentration of 0.0005 M, but almost no effective stabilization at a concentration of 0.0001 M. The control sample had almost no thermal stability under the experimental conditions.

The interferon of Examples 9-11 was more highly purified, and therefore less stable, than the interferon of Examples 1-8, yet the lanthanide salts provided an acceptable level of thermal stabilization at concentrations of 0.0005 M and higher.

TABLE 2

Thermal Stability of HFI-B in Presence of Lanthanide Salts at 37° C.

| Ex. | Lanthanide Salt | 0 days | 1 day | 4 days |
|---|---|---|---|---|
| 9. | Lanthanum Chloride - 0.002M | 7,500 | 4,500 (60%) | 3,500 (47%) |
|  | Lanthanum Chloride - 0.0005M | 5,000 | 1,600 (32%) | 800 (16%) |
|  | Lanthanum Chloride - 0.0001M | 5,000 | 1,600 (32%) | 450 (9%) |
| 10. | Gadolinium Chloride - 0.002M | 7,500 | 5,000 (67%) | 5,000 (67%) |
|  | Gadolinium Chloride - 0.0005M | 5,000 | 5,000 (100%) | 3,400 (68%) |
|  | Gadolinium Chloride - 0.0001M | 3,500 | 1,200 (34%) | 450 (13%) |
| 11. | Ytterbium Chloride - 0.002M | 5,000 | 3,500 (70%) | 1,900 (38%) |
|  | Ytterbium Chloride - 0.0005M | 5,000 | 1,900 (38%) | 1,500 (30%) |
|  | Ytterbium Chloride - 0.0001M | 5,000 | 1,500 (30%) | 450 (9%) |
|  | CONTROL | 2,000 | 260 (13%) | 180 (9%) |

Titer at indicated days of incubation; % of initial activity remaining shown in ( )

The solutions of Examples 9-11 and the control solutions were prepared with the same volume of stock interferon solution having an assayed activity of 2,000 units/ml.

EXAMPLE 12

While the lanthanide salts of Examples 9-11 did not provide much thermal stability at 37° C. below a 0.0005 M concentration, it was noted that neodymium chloride did provide an effective level of thermal stability when present in the final solution at a concentration as low as 0.00008 M. Under the test procedures of Examples 9-11, NdCl$_3$ yielded the following results, the "control" being the interferon in 0.05 M Tris-HCl, pH 7.2.

|  | Titer (% activity remaining) | | |
|---|---|---|---|
|  | 0 days | 1 day | 4 days |
| Neodymium Chloride - 0.002M | 10,000 | 8,000 (80%) | 7,800 (78%) |
| Neodymium Chloride - 0.0004M | 10,000 | 4,100 (41%) | 2,800 (28%) |
| Neodymium Chloride - 0.00008M | 10,000 | 3,000 (30%) | 2,900 (29%) |
|  | 5,200 | 700 (13.5%) | 700 (13.5%) |
| Control | | | |

All solutions of Example 12 were prepared with the same volume of stock interferon solution having an assayed activity of 5,200 units/ml.

EXAMPLES 13-20

The lanthanide salts also effectively stabilize the HFI-A against mechanical inactivation. The interferon solution was mixed with various lanthanide chloride solutions to generate final solutions containing 0.002 M lanthanide salts and buffered with 0.05 M Tris-HCl pH 7.2. The samples were subjected to the mechanical stress procedure described in part (d) above for a period of 2 minutes. The data are reported in Table 3, in which the "control" solution was the HFI-A buffered with 0.05 M Tris-HCl, pH 7.2.

All of the lanthanides at 0.002 M concentration very effectively preserved the interferon activity, but most of its activity was lost when no lanthanide was present.

When the HFI-A was tested for mechanical stability by the same test after being mixed with NaCl at various concentrations up to as high as 2 M, no stabilization was observed. Consequently, the stabilizing effects shown in Table 3 are considered to result from the presence of the lanthanide cations.

TABLE 3

Mechanical Stability of HFI-A in Presence of Lanthanides

| Ex. | Lanthanide Salt - 0.002M | 0 min. | 2 min. |
|---|---|---|---|
| 13. | Lanthanum Chloride | 4,200 | 4,200 (100%) |
| 14. | Cerium Chloride | 4,200 | 1,500 (36%) |
| 15. | Neodymium Chloride | 4,200 | 4,200 (100%) |
| 16. | Samarium Chloride | 5,000 | 4,200 (89%) |
| 17. | Gadolinium Chloride | 5,000 | 3,500 (70%) |
| 18. | Dysprosium Chloride | 5,000 | 4,200 (84%) |
| 19. | Erbium Chloride | 4,200 | 3,500 (83%) |
| 20. | Ytterbium Chloride | 4,200 | 3,500 (83%) |
|  | CONTROL | 1,500 | 210 (14%) |

Titer after indicated time of agitation; % of initial activity remaining after agitation shown in ( )

The solutions of Examples 13-20 and the control solutions were prepared with the same volume of stock interferon solution having an assayed activity of 1,500 units/ml.

EXAMPLE 21

We have found calcium to be a useful stabilization agent for interferons as it exhibits the same effects as the lanthanide salts although higher concentrations should be used.

HFI-A in a 0.05 M Tris-HCl buffer, pH 7.2, when tested for thermal stability at 37° C. by heating for 4 days was found to have retained only 2% of its biological activity. However, after the same solution was heated for 4 days under the same conditions with 1 M $CaCl_2$ the interferon retained all of its activity, and when heated with 0.5 M $CaCl_2$ added it retained 10% of its activity.

Lanthanide and calcium salts other than chlorides are also effective in stabilizing interferons and may be used in the practice of this invention. Example 22 demonstrates the effect of lanthanum acetate with respect to thermal stability and Example 23 shows its effect as to mechanical stability.

EXAMPLE 22

Solutions of human fibroblast interferon—Lot A of part (a)(1) above containing lanthanum acetate at the indicated concentrations were prepared as listed below in a Tris-HCl buffer at pH 7.2. The antiviral activity of the HFI-A was measured after the solutions were prepared and after 4 days of heating at 37° C. under the thermal stability test described above. The percent of activity remaining after 4 days of such heating is listed below. The "control" was a solution of the HFI-A in Tris-HCl buffer at pH 7.2 without any lanthanum acetate.

| Lanthanum Acetate Concentration | % Interferon Activity Remaining |
|---|---|
| 0.05M | 100% |
| 0.01M | 100% |
| 0.002M | 50% |
| 0 (Control) | less than 5% |

EXAMPLE 23

The human fibroblast interferon HFI-A was tested for stability against mechanical stress by subjecting samples to the procedure described in part (d) above for a period of 2 minutes. The interferon in 0.05 M Tris-HCl, pH 7.2, lost more than 95% of its activity after the mechanical agitation.

When lanthanum acetate was added to the HFI-A, however, from 50–100% of its antiviral activity was retained in solutions with a lanthanum acetate concentrations of 0.002 M and greater when subjected to the same mechanical stress. The solutions were buffered with 0.05 M Tris-HCl, pH 7.2. The data are presented in Table 4.

TABLE 4

Mechanical Stability of HFI-A

| Solution | Titer after indicated time of agitation; % of initial activity remaining after agitation shown in ( ) | |
|---|---|---|
| | 0 | 2 min. |
| HFI-A + 0.05M Tris-HCl | 3,000 | 115 (3.8%) |
| HFI-A + 0.01M Lanthanum Acetate | 3,800 | 3,600 (94.7%) |
| HFI-A + 0.005M Lanthanum Acetate | 3,800 | 2,700 (71.0%) |
| HFI-A + 0.002M Lanthanum Acetate | 6,500 | 3,700 (56.9%) |
| HFI-A + 0.001M Lanthanum Acetate | 3,700 | 140 (3.8%) |
| HFI-A + 0.0005M Lanthanum Acetate | 3,700 | 90 (2.4%) |

All solutions of Table 4 were prepared with the same volume of stock interferon solution having an assayed activity of 3,000 units/ml.

EXAMPLE 24

The lanthanide and calcium salts are effective stabilization agents for interferons other than the HFI-A examined in Examples 1–23.

Solutions of the human leukocyte interferon HLI described in part (a)(3) above and various concentrations of several lanthanide salts buffered with 0.05 M Tris-HCl at pH 7.2 were tested for thermal inactivation by heating at 50° C. for 4 days. The data are reported in Table 5, wherein "control" refers to the same interferon tested with only the 0.05 M Tris-HCl buffer, pH 7.2. Significant protection against inactivation was obtained, although not to the same extent found with the HFI-A.

When the same test was repeated with neodymium chloride, it was found that the neodymium was a more effective stabilizer for HLI than the salts shown in Table 5 as indicated by the data of Table 6.

The HLI also retained 3% of its activity after 5 days of heating at 56° C. when in a solution containing 1 M $CaCl_2$ buffered at pH 7.2 with Tris-HCl chloride whereas no activity was detectable in the control sample of HLI that had no $CaCl_2$.

The mouse interferon described previously in part (a)(4) retained 100% of its activity after heating for 3 days at 37° C. in a solution containing 1 M $CaCl_2$ buffered at pH 7.2 with Tris-HCl chloride and 61% of its activity after 5 days of such heating; no activity was recovered in the control sample containing no $CaCl_2$ after 5 days of heating.

The immune induced human interferon of part (a)(5) above retained 100% of its activity after 3 days of heating at 37° C. when in a solution containing 1 M $CaCl_2$ buffered at pH 7.2 with 0.05 M Tris-HCl chloride while the control samples of the interferon lost 71% of their activity during the same treatment.

TABLE 5

Thermal Stability of Human Leukocyte Interferon

| | Titer at indicated days of incubation % of remaining activity shown in ( ) | | |
|---|---|---|---|
| | 0 days | 1 day | 4 days |
| Lanthanum Chloride - 0.002M | 120,000 | 40,000 (33%) | 4,200 (3.5%) |
| Lanthanum Chloride - 0.005M | 62,000 | 18,000 (29%) | 1,000 (1.6%) |
| Gadolinium Chloride - 0.002M | 62,000 | 17,000 (27.4%) | 4,000 (4.9%) |
| Gadolinium Chloride - 0.005M | 81,000 | 12,000 (14.8%) | 4,000 (4.9%) |
| Ytterbium Chloride - 0.002M | 120,000 | 38,000 (31.6%) | 12,000 (10.0%) |
| Ytterbium Chloride - 0.005M | 81,000 | 38,000 (46.9%) | 17,000 (20.9%) |

TABLE 5-continued

Thermal Stability of Human Leukocyte Interferon

|  | Titer at indicated days of incubation % of remaining activity shown in ( ) | | |
|---|---|---|---|
|  | 0 days | 1 day | 4 days |
| CONTROL | 38,000 | 4,000 (10.5%) | 42 (0.1%) |

All solutions of Table 5, including the control solutions, were prepared with the same volume of stock interferon solution having an assayed activity of 38,000 units/ml.

TABLE 6

Thermal Stability of Human Leukocyte Interferon

|  | Titer at indicated days of incubation % remaining activity shown in ( ) | | |
|---|---|---|---|
|  | 0 days | 1 day | 3 days |
| Neodymium Chloride - 0.01M | 210,000 | 30,000 (14.3%) | 59,000 (28.0%) |
| Neodymium Chloride - 0.002M | 165,000 | 59,000 (35.8%) | 59,000 (35.8%) |
| Neodymium Chloride - 0.0004M | 155,000 | 46,000 (29.7%) | 43,000 (27.7%) |
| CONTROL | 59,000 | 6,000 (10.2%) | 7,200 (12.2%) |

All solutions of Table 6, including the control solutions were prepared with the same volume of stock interferon solution having an assayed activity of 59,000 units/ml.

EXAMPLE 25

Our test data further indicate that the lanthanide and calcium salts can stabilize interferons for long periods of time when stored at elevated temperatures.

HFI-B was tested for long term storage at 37° C. with the addition of lanthanum, gadolinium and ytterbium chlorides buffered at pH 7.2 with 0.05 M Tris-HCl. Ytterbium chloride completely stabilized the interferon for 18 days and approximately 10% of its activity was recoverable after 46 days. Gadolinium and lanthanum chlorides were less effective, but the former provided useful protection for 26 days and the latter for 11 days. The data are reported in Table 7, in which "control" refers to the interferon buffered at pH 7.2 with 0.05 M Tris-HCl and the concentration of the lanthanide salt was its concentration in solution with the interferon.

TABLE 7

Long Term Stabilization of Human Fibroblast Interferon at 37° C.

|  | Titer at indicated days of incubation; % remaining activity shown in ( ). | | | |
|---|---|---|---|---|
| Days | LaCl$_3$ 0.005M | GdCl$_3$ 0.005M | YbCl$_3$ 0.005M | Control |
| 0 | 22,000 | 54,000 | 88,000 | 16,000 |
| 1 | 16,000 (72%) | 47,000 (87%) | 100,000 (114%) | 2,100 (13%) |
| 4 | 16,000 (72%) | 16,000 (30%) | 100,000 (114%) | 1,200 (7.5%) |
| 11 | 5,600 (26%) | 22,000 (41%) | 100,000 (114%) | <250 |
| 18 | 720 (3.3%) | 10,000 (18.5%) | 100,000 (114%) | <250 |
| 26 | <250 | 5,400 (10%) | — | <250 |
| 32 | <250 | 400 | 8,000 (9%) | <250 |
| 39 | <250 | 400 | 16,000 (18%) | <250 |
| 46 | <250 | 1,200 | 12,000 (13.4%) | <250 |

All solutions of Table 7, including the control solutions, were prepared with the same volume of stock interferon solution having an assayed activity of 16,000 units/ml.

EXAMPLE 26

Tris-HCl buffer at pH 7.2 was used in preceding Examples. However, the lanthanide and calcium acid salts can be mixed with interferons using other compounds as buffers and at a pH other than 7.2 to provide for stabilization of the interferons.

A series of experiments were performed using a solution of HFI-B containing lanthanum chloride at 0.002 M as the stabilizing agent with 3 compounds as buffers at 5 pH levels. The various solutions were subjected to the thermal stability test at 37° C. for 5 days. The data are assembled in Table 8, in which the "control" entries refer to the HFI-B in the various buffers but without the lanthanum chloride. Lanthanum chloride provided useful stabilization of the interferon in all 3 buffers over a pH range of 3.0 to 9.0.

TABLE 8

Thermal Stability of HFI-B at 37° C. in Various Buffers and Various pH Levels in the Presence of Lanthanum Chloride

| Stabilizing Agent | Buffer | pH | Titer at indicated days of incubation % of remaining activity shown in ( ) | | |
|---|---|---|---|---|---|
|  |  |  | 0 days | 1 day | 5 days |
| 0.002M LaCl$_3$ | 0.05M glycine-HCL | 3.0 | 15,500 | 12,500 (81%) | 12,500 (81%) |
| None-Control | 0.05M glycine-HCL | 3.0 | 12,500 | 640 (5%) | 640 (5%) |
| 0.002M LaCl$_3$ | 0.05M KCl-Borate | 8.2 | 60,000 | 72,000 (120%) | 40,000 (67%) |
| None-Control | 0.05M KCl-Borate | 8.2 | 19,000 | 2,800 (20%) | 570 (4%) |
| 0.002M LaCl$_3$ | 0.01M Tris-HCl | 8.6 | 28,000 | 28,000 (100%) | 2,900 (9%) |
| None-Control | 0.01M Tris-HCl | 8.6 | 15,000 | 1,700 (11%) | 400 (3%) |
| 0.002M LaCl$_3$ | 0.05M KCl-Borate | 9.0 | 14,000 | 14,000 (100%) | 2,800 (20%) |
| None-Control | 0.05M KCl-Borate | 9.0 | 10,000 | 500 (5%) | 180 (2%) |
| 0.002M LaCl$_3$ | 0.05M KCl-Borate | 10.0 | 2,800 | 510 (18%) | 30 (2%) |
| None-Control | 0.05M KCl-Borate | 10.0 | 2,800 | 510 (18%) | 68 (1%) |

All solutions of Table 8, including the control solutions, were prepared with the same volume of stock interferon solution There has thus been described compositions of matter comprising a solution of an interferon and a soluble lanthanide or calcium salt that is effective to improve the stability of the interferon, stability against thermal and mechanical stresses being specifically discussed. As mentioned previously in this disclosure, lanthanide refers to elements of Group 3B of the Periodic Table which have atomic numbers from 57-71 inclusive, comprising the 15 elements from lanthanum through lutetium on the Periodic Table. Sodium chloride was shown to be an ineffective stabilizing agent, Examples 13-20, and other of our work established that magnesium acetate was ineffective; this leads us to the conclusion that it is cations of the compounds defined above that are responsible for the enhanced interferon stabilization reported in the examples. The lanthanide or calcium compound used to stabilize the interferons is to be a soluble salt. Various salts may be employed, other than the acetates and chlorides discussed in the examples, as long as a soluble lanthanide or calcium salt is formed that will not impair the biological activity of the interferon.

The lanthanide salts are effective stabilizing agents over a wide concentration range; a lanthanide salt concentration of about 0.002 M or higher provides effective stabilization with all of the lanthanide salts, but concentrations as low as 0.0001 M or 0.00008 M can provide useful stabilization with some lanthanide salts. Calcium salts also are effective over a broad range of concentrations but should be present at a concentration of about 0.5 M or higher. The upper limit of the concentration is determined by the solubility of the salts. The concentration of the stabilizing agent should be selected with regard to the specific interferon to which it is to be added and the degree of stabilization that is required in a particular composition. On the basis of toxicity classification, the lanthanides are considered only slightly toxic, [23], and neodymium and other rare earth salts have been used successfully as anti-coagulants. The $LD_{50}$, mg/Kg, for subcutaneous and intraperitoneal injection of lanthanum chloride in mice is 3,500 and 372.4 respectively, so that injection of 10 ml of a preparation containing 0.002 M lanthanum chloride (total $LaCl_3$ is 0.005 g) into a 160 lb. man is only 0.07 mg/Kg, far below the toxicity level reported for mice. It thus seems likely that lanthanide ions at a concentration of 0.002 M and higher would be acceptable in a preparation of interferon for human injections even if concentrated interferon stock solutions were not diluted before administration. Thus, an effective amount of the compounds can be added to interferons without reaching a level that will cause therapeutic problems.

The compositions containing an interferon and a lanthanide or calcium salt provide effective stabilization over a wide pH range. In general, a pH range of about 3.0 to 9.0 is preferred, and the pH for a particular composition should be selected with a view towards preventing insolubilization of the lanthanide or calcium salt. Various buffers, organic and inorganic, can be used to obtain the requisite pH, the limitation being that the buffer must not cause precipitation of the lanthanide or calcium salt. For example, the lanthanide and calcium salts cannot be used with phosphate buffered solutions since insoluble phosphates would be formed. The specific buffer should be one that is suitable for biological use and will not impair either the interferon or the stabilizing agent.

The enhanced stability of interferons treated with lanthanide and calcium salts in accordance with this invention will aid in the preservation of interferon activity during the various process steps involved in interferon production. The interferons can be made more stable against loss of activity when subjected to heating, agitation, or other mechanical shock, to which the fluids may be subjected during production or storage. Interferons combined with the lanthanide or calcium salts may also be employed in therapeutic treatment provided, of course, that the salt is present at a safe level below its toxicity level. Interferon preparations containing lanthanide or calcium salts can be diluted prior to administration.

Another potentially useful effect of the addition of lanthanide salts to interferons is indicated by the data included in Tables 1 through 8 and the data of Example 12. The titer of the interferon in both the control samples and the samples containing the lanthanide salts at 0 days is shown in these data. This refers to the initial activity of the interferon in the samples, and as to each respective set of data, the interferon was present in the same amount and at the same concentration for all of the samples including the control samples. These data illustrate that the addition of a lanthanide salt increases the apparent antiviral potency of the interferon. The various sets of data show this is a consistently observable trend and not a transitory phenomenon. Thus, in addition to its beneficial stabilizing effects, the addition of a lanthanide salt has the further characteristic of increasing the potency of a given quantity and concentration of interferon.

While the conclusions regarding the enhanced stability and increased activity of interferons by the addition of lanthanide and calcium salts are believed to be consistently supported by the data presented herein, we are at this time unable to define the specific mechanism that is responsible for these results. Therefore, we do not wish to be bound by any particular theory as to the manner in which lanthanide and calcium salts provide the enhanced characteristics disclosed herein.

LIST OF REFERENCES

[1] The Interferon System: A Current Review to 1978 Vol. 35, 1977, Texas Reports on Biology and Medicine.
[2] Interferons and Interferon Inducers, ed. N. B. Finter, North-Holland Publishing Co., 1973.
[3] Grossberg. Nonviral Interferon Inducers: Natural and Synthetic Products. Supra note [1] at p. 111.
[4] Cantell. The Development of Research on Interferons. Supra note [2] at p. 1.
[5] Isaacs & Lindenmann: Virus Interference, Proc. Roy. Soc. Series B, 147: 258-273, 1957.
[6] U.S. Pat. No. 3,699,222, Isaacs & Lindenmann, Production of Viral Interfering Substances.
[7] Dunnick & Galasso. Clinical Trials with Exogenous Interferon: Summary of a Meeting. Journal of Infectious Diseases, 135: p. 109-123, 1979.
[8] Interferon, Breaking the Production Bottleneck. Medical World News, Oct. 16, 1978, pp. 82-94.
[9] Galasso & Dunnick: Interferon, An Antiviral Drug for Use in Man. Supra note [1], p. 478.
[10] Sedmak & Grossberg. Stabilization of Interferon. Supra note [1], pp. 198-204.
[11] Cavalieri & Pestka. Synthesis of Interferon in Heterologus Cells etc. Supra note [1], p. 117.
[12] Edy. Large Scale Production of Human Interferon in Monolayer Cell Cultures. Supra note [1], p. 132.
[13] Cantell & Hirvonen. Preparation of Human Leukocyte Interferon for Clinical Use. Supra note [1], p. 138.

[14] U.S. Pat. No. 3,800,035, Goore, Production of Interferon from Human Leukocytes in the Absence of Serum.
[15] Berman & Vilcek, Virology 57: 378, 1974.
[16] Anfinsen et al, Proc. Nat. Acad. Sci.: USA 71:3139-42, 1974.
[17] Edy et al, J. Gen. Virol. 33:517, 1976.
[18] Cantell et al, Proc. of the Tissue Culture Association Workshop, Lake Placid, N.Y., 35-38, 1973.
[19] Jariwalla et al, Archives of Virology 49:261-272, 1975.
[20] Epstein et al, J. Immunol. 112:617-26, 1974.
[21] Jameson et al, Proc. Soc. Exp. Biol. Med 155:173-8, 1977
[22] Heine et al, Archives of Virology 57:185, 1978.
[23] Haley, Journal of Pharm. Sciences, 54:663-670, 1965.

It is claimed:

1. A composition of matter comprising a solution of an interferon and a soluble lanthanide or calcium salt as a stabilizing agent for the interferon, wherein the salt is present at a concentration of at least about 0.0005 M for lanthanide salts except for neodymium, at least about 0.00008 M for a neodymium salt, and at least about 0.5 M for a calcium salt.

2. A composition of matter comprising a solution of human fibroblast interferon and a soluble lanthanide or calcium salt as a stabilizing agent for the interferon, wherein the salt is present at a concentration of at least about 0.0005 M for lanthanide salts except for neodynium, at least about 0.00008 M for a neodynium salt, and at least about 0.5 M for a calcium salt.

3. The composition of claim 2 wherein the salt is lanthanum chloride.

4. The composition of claim 2 wherein the salt is cerium chloride.

5. The composition of claim 2 wherein the salt is neodymium chloride.

6. The composition of claim 2 wherein the salt is samarium chloride.

7. The composition of claim 2 wherein the salt is gadolinium chloride.

8. The composition of claim 2 wherein the salt is dysprosium chloride.

9. The composition of claim 2 wherein the salt is erbium chloride.

10. The composition of claim 2 wherein the salt is ytterbium chloride.

11. The composition of claim 2 wherein the salt is lanthanum acetate.

12. The composition of claim 2 wherein the salt is calcium chloride.

13. The composition of claim 2 wherein the salt is calcium acetate.

14. A composition of matter comprising a solution of a human leukocyte interferon and a soluble lanthanide or calcium salt as a stabilizing agent for the interferon, wherein the salt is present at a concentration of at least about 0.0005 M for lanthanide salts except for neodymium, at least about 0.00008 M for a neodymium salt, and at least about 0.5 M for a calcium salt.

15. The composition of claim 14 wherein the salt is lanthanum chloride.

16. The composition of claim 14 wherein the salt is gadolinium chloride.

17. The composition of claim 14 wherein the salt is ytterbium chloride.

18. The composition of claim 14 wherein the salt is neodymium chloride.

19. The composition of claim 14 wherein the salt is calcium chloride.

20. A composition of matter comprising a solution of a mouse interferon and a soluble lanthanide or calcium salt as a stabilizing agent for the interferon, wherein the salt is present at a concentration of at least about 0.0005 M for lanthanide salts except for neodymium, at least about 0.00008 M for a neodymium salt, and at least about 0.5 M for a calcium salt.

21. The composition of claim 20 wherein the salt is calcium chloride.

22. A method for stabilizing interferon in solution comprising adding a soluble lanthanide or calcium salt to the interferon in solution, wherein the salt is present at a concentration of at least about 0.0005 M for lanthanide salts except for neodymium, at least about 0.00008 M for a neodymium salt, and at least about 0.5 M for a calcium salt, and adding a buffer to said solution and maintaining a pH such as will retain the lanthanide or calcium salt in solution.

* * * * *